United States Patent [19]

Lewis, Jr.

[11] Patent Number: 4,459,979

[45] Date of Patent: Jul. 17, 1984

[54] ANTILORDOSIS BELT

[76] Inventor: Royce C. Lewis, Jr., 3801 21st St., Lubbock, Tex. 79410

[21] Appl. No.: 419,060

[22] Filed: Sep. 16, 1982

[51] Int. Cl.³ .............................................. A61F 5/02
[52] U.S. Cl. .................................................... 128/78
[58] Field of Search ...................... 128/78, 95, 75, 99, 128/96, 686, 69, DIG. 15; 2/44, 338, 321, 336, 340, 322; 273/54 B; 24/306, 316, 182, 197, 200; 182/3-9

[56] References Cited

U.S. PATENT DOCUMENTS

| | | | |
|---|---|---|---|
| 2,181,689 | 11/1939 | Bell | 128/78 |
| 2,372,034 | 3/1945 | Versoy | 128/96 |
| 3,434,469 | 3/1969 | Swift | 128/78 |
| 3,850,164 | 11/1974 | Hare | 128/75 |
| 4,245,628 | 1/1981 | Eichler | 128/78 |

Primary Examiner—Richard J. Apley
Assistant Examiner—Harry Macey
Attorney, Agent, or Firm—Marcus L. Bates

[57] ABSTRACT

An orthopedic appliance of resilient material conforming to the lower back of a person and held in proper position by a waist band. The antilordosis belt device improves ones posture and prevents back injury to the lower back while lifting by reinforcing the muscles associated with the lower spine without unduly interferring with one's normal articulated freedom of motion. The body supporting device prevents increased lordosis by the provision of a relatively wide front belt which girdles the front of the abdomen, and three back belts which extend from attachment at the terminal ends of the abdomen belt and girdles the rear or back of the body. The three rear belts are made up of straps, and comprise a rear belt of medium width which fits above the small of the back and two small belts which fit over the hips. The hip belts, back belts, and abdomen belt all cooperate together to form a triangular support system so that when a person tends to tilt into a sway back position, the resultant forces are resolved along the sides of the triangle to prevent injury to the lower back, thereby significantly obviating any increase in lordosis.

11 Claims, 10 Drawing Figures

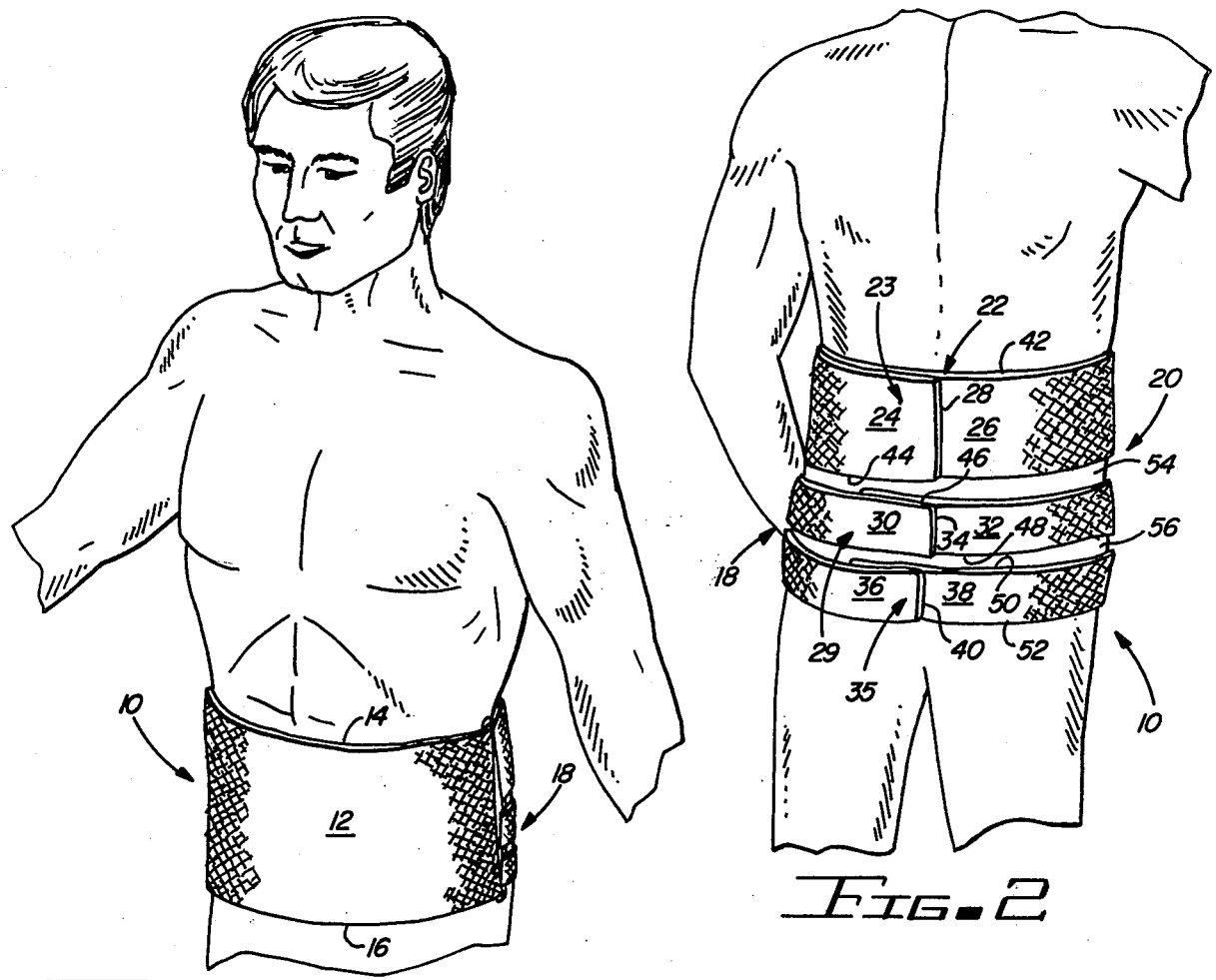
FIG-1
FIG-2
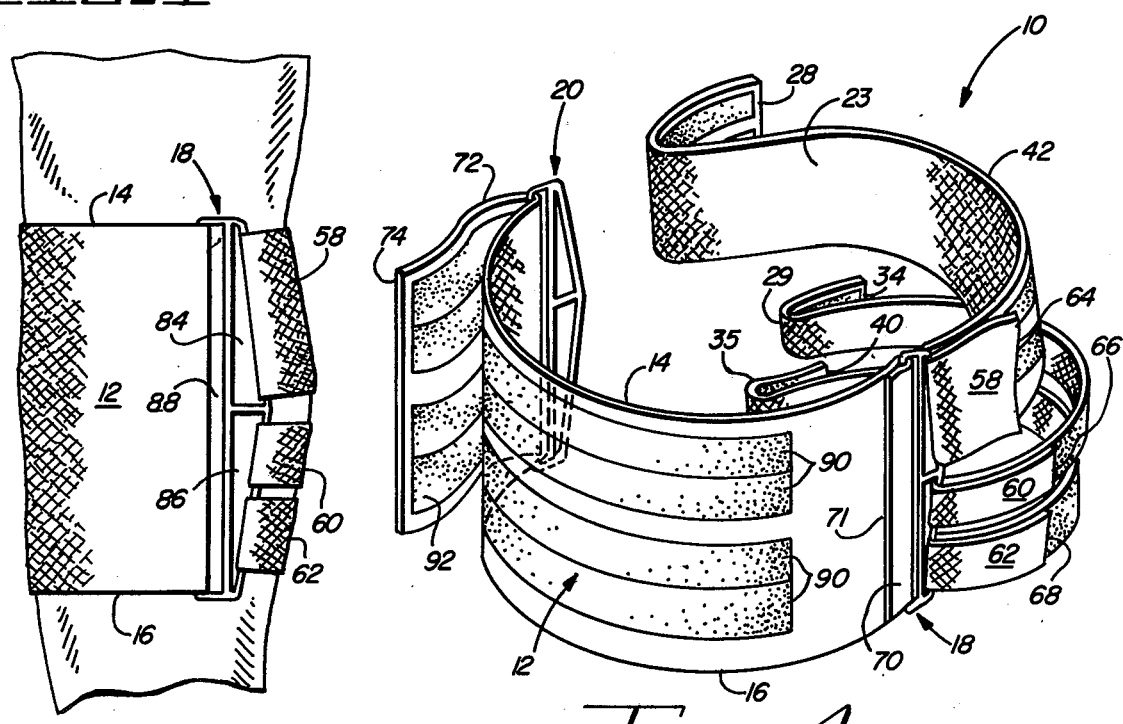
FIG-3
FIG-4

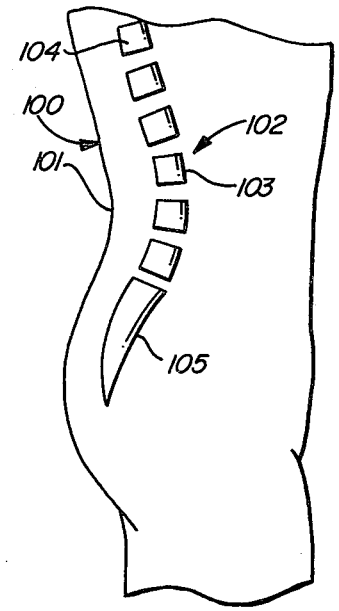
FIG. 8 (PRIOR ART)
NORMAL POSTURE
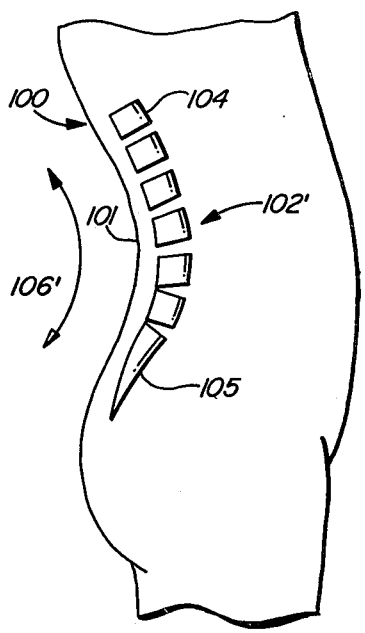
FIG. 9 (PRIOR ART)
INCREASED LORDOSIS WHEN LIFTING
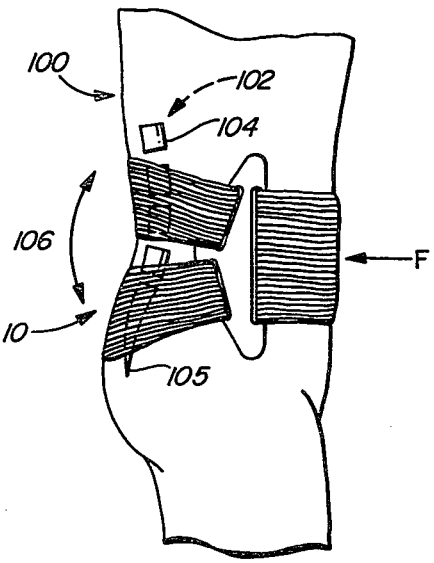
FIG. 10 (IMPROVEMENT)
PREVENTION OF INCREASED LORDOSIS

ANTILORDOSIS BELT

BACKGROUND OF THE INVENTION

Most lower back pain is brought about by movement which occurs in the lower back while improperly lifting excessive weights, and is especially predominant in those persons having more than an average degree of curvature (lordosis) in the lower back. Such a person is unusually susceptible to strain and if injury or repeated stress to the cartilage disc occurs, severe disability may result with a painful catch in the low back and intense pain in the back of the leg. As pointed out in "Care of the Back", Industrial Edition Two by Ishmael and Shorbe, J. P. Lippincott Co., Philadelphia, Pa.) to which reference is made for further background of this invention, there are several configurations of posture which can be employed to reduce the likelihood of straining the back.

After one has strained his back, it is possible to employ various different orthopedic appliances, such as seen in U.S. Pat. Nos. Swift 3,434,469; Rosenburg 4,175,553; Johnson 3,717,143; Romano 4,135,503; Draves 1,924,640; Norman 3,087,496; Boone 2,412,075; Gaylord 3,568,670; Martinee 1,634,621; and Schrieber 3,052,236; to which reference is made for further background of the invention. These devices, when worn, add support to the spinal column and partially limit the free movement of the back. Most prior art back braces or back support devices are usually in the form of a large, body encircling, belt-like appliance which conforms to the abdomen and the back and which is reinforced in selected places to achieve the desired results. U.S. Pat. Nos. Berkeley 4,080,962 and Bell 2,181,689 employ back braces which include spaced apart body encircling belts, as well as fore and aft abdomen and back conforming pads connected together by belts.

As pointed out in the Ishmael, et al publication, it is possible to strengthen the spinal column by undergoing specific physical exercise, and furthermore, it is possible to employ posture training in order to avoid lower back fatigue. As pointed out in the above U.S. Patents, it is possible to employ a back brace or back support in order to reduce the strain on the back after damage thereto has occurred.

It would therefore be desirable to have made available an orthopedic appliance in the form of a back support device which could be worn by those persons susceptible to inceased lordosis. Such an antilordosis belt could also be worn by those who have a history of back ailments. More importantly, such a belt could be worn by anyone engaged in the type of physical labor which is condusive to increased lordosis. An antilordosis belt which achieves these desirable attributes and goals is the subject of the present invention.

SUMMARY OF THE INVENTION

The present invention provides an antilordosis apparatus in the form of a back support device. The apparatus of the present invention comprises a relatively flexible, wide front belt which girdles the abdomen of the wearer, and further includes a back belt support assembly attached to the front belt by special side brace attachments which cooperate together to direct the line of force brought about by belt tension in specific predetermined directions so that the wearer of the belt support device is less susceptible to increased lordosis (inward curvature of the lower spine).

The back belt support assembly has opposed ends thereof attached to the opposed ends of the front belt by means of side brace attachments. The side brace attachments extend vertically respective to the wearer and provides both a fastener means and an alignment means. The side brace attachments enable the front belt to be adjusted in circumference as well as enabling the back belt support assembly to be adjusted respective to the front belt. The side brace attachments further maintain each of the back belts separated from one another and aligned along a predeterimed circumferentially extending line so that the tension induced into each of the belts, as a person changes his posture, is resolved along a predetermined path.

The back belt support assembly includes an upper belt, a central belt, and a lower belt, with the lower belt and central belt being of relatively small width; the upper belt being of medium width, and the front belt being relatively larger in width.

The side brace attachments are in the form of an elongated built-up framework having an elongated, longitudinally extending slot formed forwardly therein for attachment to the opposed sides of the front belt, with there being vertically spaced adjacent apertures located rearwardly and next to the slot. The adjacent apertures are formed by a bent bar, about which a marginal terminal end of the back belts are secured. The upper back belt opposed marginal ends are received within the upper aperture of the opposed side braces, while the opposed marginal ends of the remaining two back belts are received within the remaining apertures of the side braces. The bent bar orients each of the back belts respective to one another, maintains the belts separated from one another, and resolves the tension induced into the back belt into the front belt in a manner whereby loads placed on the lower back during movement thereof are resisted in a manner which encourages the wearer of the belt to avoid positioning the lower spine in a location which may increase lordosis, and, at the same time, reinforces the lower spine and back muscles so that the likelihood of injury thereto is further reduced. The belt device therefore inherently trains the wearer thereof to avoid those positions of posture which increase lordosis.

According, a primary object of the present invention is the provision of an antilordosis belt which can advantageously be worn by those persons who are susceptible to straining the small of the back.

Another object of the invention is the provision of an antilordosis belt having a relatively large abdomen conforming belt to which there is attached a plurality of spaced apart back belts which conform to the lower back, and which are attached to one another in a manner to transfer loads imposed thereon due to poor posture thereby reinforcing the weak area of the back and reducing the likelihood of increased lordosis.

A further object of the present invention is the provision of an antilordosis belt having side brace attachments by which a plurality of back belts are connected to a large front belt in a new and unusual manner and which brings about unexpected results.

A still further object of this invention is the provision of an orthopedic appliance in the form of a back support device which includes a front belt attached to a plurality of back belts, wherein the back belts transfer undesirable pain inducing loads into the front belt and to the muscles of the abdomen.

Another and still further object of the present invention is the provision of an antilordosis belt asembly having a front belt connected to a plurality of back belts by special side brace attachment means which directs the lines of force induced into the back belts along predetermined paths so that the lower back of the wearer is reinforced and strengthened in areas of weakness.

An additional object of the present invention is the provision of a back support device having a front belt which conforms to the abdomen attached to a plurality of back belts by opposed side brace attachment means which jointly cooperate together in a manner to strengthen and reinforce the lower back, while at the same time the support device restrains a person from placing his anatomy into a position to further complicate lordosis.

These and various other objects and advantages of the invention will become readily apparent to those skilled in the art upon reading the following detailed description and claims and by referring to the accompanying drawings.

The above objects are attained in accordance with the present invention by the provision of a combination of elements which are fabricated in a manner substantially as described in the above abstract and summary.

BRIEF DESCRIPTION OF THE DRAWINGS

FIG. 1 is a front perspective view of a back support device made in accordance with the present invention, operatively attached to the anatomy of a person;

FIG. 2 is a rear perspective view of the illustration of FIG. 1;

FIG. 3 is an enlarged, side view of the illustration seen in FIGS. 1 and 2;

FIG. 4 is a perspective view of a back support device seen illustrated in FIGS. 1-3;

FIGS. 8 and 9 are diagrammatical representations which show the spine of a prior art human anatomy in different degrees of curvature; and, FIG. 10 is a diagrammatical representation of the anatomy of FIGS. 8 and 9 together with the back support device of FIGS. 1-7.

DETAILED DESCRIPTION OF THE PREFERRED EMBODIMENTS

Figure 7:
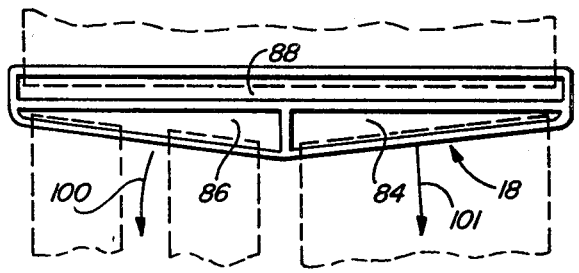
FIG. 7 is a detailed view of part of the back support device seen illustrated in the foregoing figures.

In FIG. 1 of the drawings, there is illustrated an orthopedic appliance 10, hereinafter referred to as a back support device, operatively attached to the anatomy of a person. The back support device comprises a relatively wide front belt 12 having an upper circumferentially extending edge portion 14 and a lower circumferentially extending edge portion 16 spaced from the upper edge portion. The front belt terminates in attached relationship respective to a side brace attachment 18.

As seen illustrated in FIG. 2, together with other figures of the drawings, another side brace attachment 20, identical to side brace attachment 18 is attached at the terminal end of the other side of the front belt.

The side brace attachments are positioned substantially vertical respective to the anatomy of a person. The details of the side brace attachment will be more fully discussed later on in this disclosure.

In FIGS. 2-4, numeral 22 indicates a back belt assembly which forms part of the back support device of the present invention. The back belt assembly includes an upper belt 23 of medium width respective to the other belts. The upper belt includes marginal ends 24, 26, which overlap one another when fastened together, thereby presenting one terminal end 28 exposed as illustrated in FIG. 2 of the drawings. A central belt 29 of relatively small width includes marginal end portions 30, 32 which overlap one another when fastened together, thereby leaving one terminal end 34 exposed. A lower belt 35 of substantially the same width as belt 29 includes marginal end portions 36, 38 which overlap one another when fastened together, thereby presenting terminal end 40.

Figure 5:
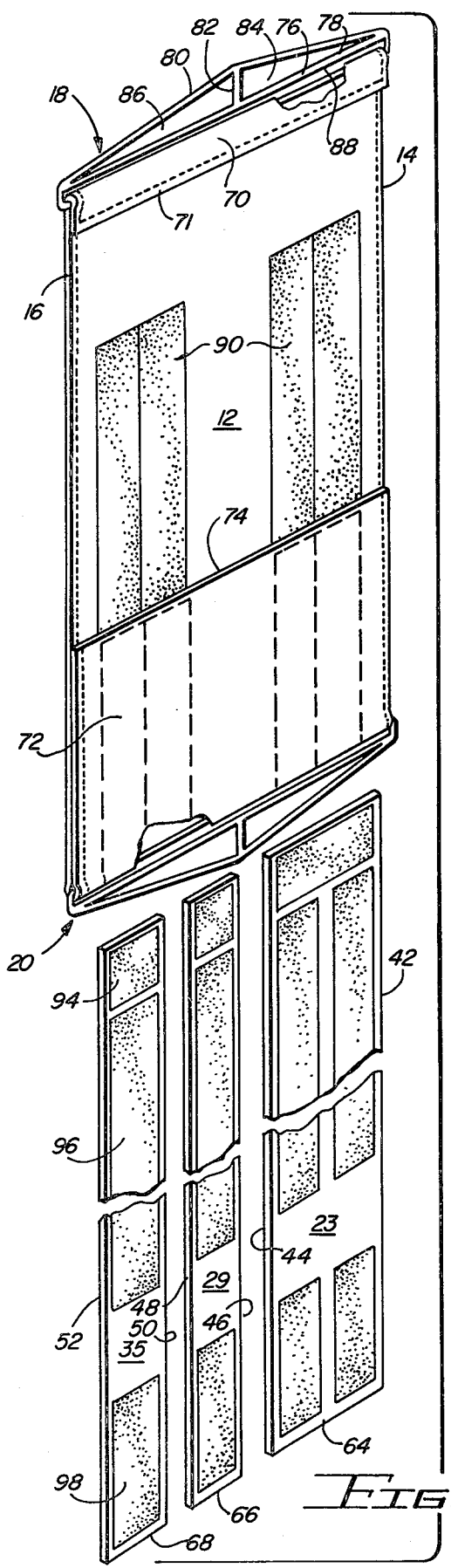
FIG 5 is a partially broken, disassembled view of the back support device seen illustrated in FIG. 4.
Figure 6:
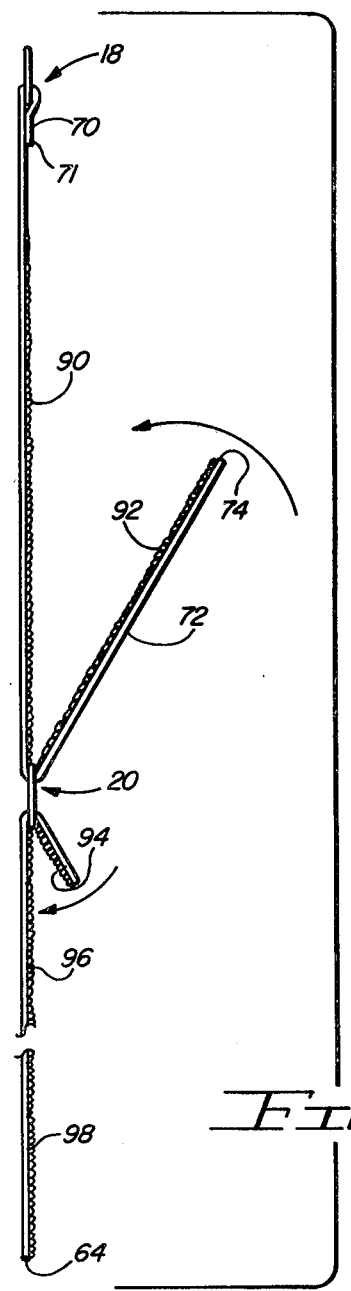
FIG. 6 is an edge view of the back support device seen illustrated in the foregoing figures.

Numeral 42 of FIGS. 2, 4, and 5, indicates the uppermost circumferentially extending edge of the back belt assembly, which is comprised of the before mentioned overlapping marginal ends of belt 23. Numeral 44 indicates the lower edge of belt 23. Numeral 46 indicates the upper circumferentially extending edge of central belt 29, while numeral 48 indicates the lower edge of the central belt 29. Numeral 50 indicates the upper edge of belt 35 while numeral 52 indicates the lower edge of the lower belt 35, as well as the lowermost edge of the back belt assembly. The back belts are each spaced from one another, thereby leaving a space or slot 54 and 56 between adjacent back belts.

In FIG. 4, together with other figures of the drawings, numerals 58, 60, and 62, respectively, illustrate other marginal end portions of the upper, central, and lower belts 23, 29, and 35, respectively, which have been inserted through the side brace attachments and secured back up on itself by means of Velcro fasteners, as will be more fully discussed later on in this disclosure.

In FIG. 4, together with other figures of the drawings, numerals 64, 66, and 68, respectively, illustrate other terminal ends of the upper, central, and lower belts, respectively, of the back belt assembly. As seen in FIG. 5, the front belt has a marginal end portion 70 which is inserted through the side brace attachment 18, brought back upon itself, and stitched together at a location adjacent to terminal end 71 thereof, thereby leaving a marginal free end at 72 which is brought back upon itself and removably secured in the manner illustrated in the drawings. Numeral 74 indicates the terminal end of the free end of the front belt.

The side brace attachments 18 and 20 of FIG. 5 each comprise a built-up, open metal framework having rearwardly and forwardly spaced adjacent apertures which receive the marginal ends of the various belt, and maintains each of the belts properly oriented respective to one another, so that the loads imposed upon each of the belts are directed along specific lines of force to reduce the likelihood of increased lordosis. In particular, side brace attachments 18 and 20 each comprise parallel tubular members 76 and 78 which are spaced from one another and attached together in spaced relationship at the opposed ends thereof, and which are also attached to a rearwardly bent bar 80. Spacer bar 82 maintains the relationship of and transfers loads between the various different bars. The bars cooperate together to present forwardly directed apertures 84, 86 which are disposed rearwardly of a relatively side adjacent slot 88. This configuration of the side brace attachments enables the marginal end 70 of the front belt to be roved through the slot 88 and permanently affixed back upon itself in the illustrated manner of FIG. 5, while the apertures 84 and 86 of each of the side brace attachments confront one another rearwardly, with the slots 88 on each of the side brace attachments confronting one another in a forward direction, when the side brace attachments are positioned at opposed sides of the anatomy, as seen illustrated in FIGS. 1-3.

Velcro fastener material 90, 92, 94, 96, and 98 is placed in the illustrated strategic areas on each of the belt surfaces so that the marginal ends of each of the belts can be brought back upon itself and releasably fastened in the illustrated manner of the FIGS. of the drawings. In particular, for example, velcro fastener material 90 can be loops, while velcro material 92 is hooks, or vice versa. Likewise, the material at 94 can be loops while the material at 96 is hooks, or vice versa. The material at 64 can be loops, while the material at 98 is hooks, for example.

It is considered within the comprehension of this invention to bring the marginal ends 58, 60, and 62; respectively; of belts 23, 29 and 35; respectively; through the apertures of the side brace attachment and stitch the marginal ends back upon themselves in the same illustrated manner seen at 70, 71 in FIG. 5, for example, thereby eliminating the need for the Velcro fastener material being applied at one side of the back belt assembly. Adjustment of the various belts can be satisfactorily achieved with such a configuration of the invention.

In the preferred embodiment of the invention illustrated in the drawings hereof, the front belt if placed about the abdomen with the uppermost edge 14 being placed in overlying relationship respective to the lowermost rib of a persons rib cage. This places the lower edge 16 of the front belt in near contrast with the upper legs when a person wearing the belt is seated, for example. The side brace attachemnt 18 is properly positioned in vertically aligned relationship in proximity of one's hip and at approximately the mid-way position of the trunk. The marginal end 72 of the front belt is adjusted so that the opposed side brace attachment is similarly positioned at the opposed side of the body, and the velcro fasteners 90, 92 are engaged with one another.

The back belt assembly is then properly fastened about the back by first overlapping marginal ends 58, 50, 62 in the illustrated manner of FIGS. 3 and 4, and thereafter marginal ends 24, 30, 36 are roved through the two adjacent apertures 84, 86 and the velcro fastening material 98 is brought back upon and fastened to the Velcro material 96 as the back belts are tensioned. The belt now conforms to the curvature of one's anatomy, and the belts can be individually tightened while simultaneously contorting the anatomy in various different configurations in order to facilitate attaining the desired tension in each of the back belts.

It will be noted in FIG. 7 that the arrows at 100, 101 diverge from one another. The divergence of the opposed side brace attachment members therefore orient the upper belt 23 in an upper direction as the belt circumscribes the back from the position above the hips towards the spine where the uppermost belt then commences to descend back down towards the hips because of the symmetry of the back support device and because of the indentical opposed side brace attachments.

The central and lower belts 29, 35 are maintained parallel to one another and are both directed along a line 101 which diverges respective to the upper belt and therefore the lower and central belts as the belts leave the aperture 86, and are thereby oriented in spaced relationship respective to the upper belt so that the lowermost belt is brought about the cheeks of the buttocks while the central belt is maintained properly positioned in spaced relationship respective to the uppermost and lowermost belt, thereby leaving space 54, 56 between the adjacent belts of the back belt assembly.

Therefore, the side brace attachment provides means by which the front belt and back belt assemblies are adjustably affixed to one another in a removable manner. The side brace attachments maintain the various different belts properly oriented respective to one another and to one's anatomy so that when the belts are properly tensioned respective to one another, movement of the lower spine is restrained in a manner to reinforce the muscles of the back and preclude back strain, and thereby reduce lordosis. The back support device resolves loads imposed thereon along a triangular system of forces, with the side brace attachments being the apex of the triangle, the spine being the base of the triangle, and adjacent back belts 23 and 29 being the side of the triangle, as seen illustrated by numerals 100, 101, in FIG. 7. Accordingly, should one improperly bend while lifting, the induced forces occasioned by movement of the anatomy in order to achieve the bending are resolved between the spaced belts of the back belt assembly with the forces being transferred into the side brace attachments and then resolved into the front belt where the wide front belt transfers the resolved forces over a large area of the stomach muscles.

The back support device of the present invention is especially adapted to prevent increased lordosis among those having previously strained the back, and more especially discourages those with excessive curvature of the spine from engaging in physical activities which are likely to induce back strain. The belt also reinforces the critical areas associated with the small of the back, so that a working person subject to back strain is capable of more endurance, thereby working more efficiently because of the relief of the back pain.

Accordingly, the present invention comprehends a back support device 10 having a flexible relatively wide front belt 12 which girdles the abdomen of the wearer thereof and includes an upper and lower edge portion 14 and 16 which terminates in attached relationship at 18, 20 respective to a back belt assembly 22.

The back belt support assembly includes an upper belt 23, a central belt 29, and a lower belt 35. Means 18 and 20 maintain the belts spaced from one another and connected to the front belt so that forces induced into the small of the back as a result of bending of the spine are transferred through one or more of the belts of the back belt assembly, into the attachments 18 and 20 and into the front belt assembly.

The side brace attachment preferably is made of relatively stiff or tempered wire $\frac{1}{8}$-5/32 inch diameter welded and bent up into the configuration illustrated in the drawings. The side brace attachment could also be made by stamping the slot and aperture into a light weight piece of metal.

The belt is made of woven light weight canvas material which is doubled and stitched to increase the self-support characteristics thereof. This material is also referred to as medium weight duck fabric. There are many synthetics which are suitable for fabrication of the belt device, both solids and woven.

FIGS. 8-10 diagrammatically disclose the anatomy of a human 100'. The small of back is generally indicated by the numeral 101. The vertebrae which make up the lower spinal column 102 are shown in the drawings. In FIG. 8, there is disclosed the configuration of the spinal column of a person having normal posture. In FIG. 9, there is disclosed the configuration of the spinal column of a person suffering from swayback, or increased lordosis. FIG. 10 illustrates the manner in which the antilordosis belt of the present invention prevents increased lordosis.

The lower spinal column normally curves rearwardly from area 103, as noted at 104 and 105. Lifting increases this curvature, as noted at 106'. The belt device 10 of the present invention provides an opposing force 106 which is provided by the back belt assembly of this invention. This opposing force is transferred into the opposed sides of the front belt 12 to thereby provide the indicated opposing force F. This provides the opposing force at 106, and reduces lordosis from 106' to thereby restrain the back from assuming the configuration of FIG. 9. This unique action forces the spinal column into the preferred and normal configuration of FIG. 8. Hence, the present invention provides a means by which increased lordosis is avoided, as contrasted to prior art devices which aim to cure the increased lordosis after the back has been injured.

I claim:

1. A back support device comprising a flexible relatively wide front belt and a plurality of back belts; said front belt is for girdling the abdomen of the wearer thereof; said front belt has a width defined by an upper and lower edge portion, said front belt terminates at opposed sides; said plurality of back belts jointly define a back belt assembly, said back belt assembly includes an upper and lower edge, and opposed sides; a side brace attachment connected to each of the opposed sides of said front belt and each of the opposed sides of the back belt assembly so that each back belt is releasably connected to said opposed sides of said front belt to thereby enable the back support device to be removed from the wearer thereof;

said back belt assembly of said back support device includes an upper belt, a lower belt, and a central belt with said central belt being located between the upper and lower belts; said upper, lower, and central belts can be spaced from one another;

said side brace attachment is a relatively inflexible elongated planar frame comprising rod-like members and extends parallel to said opposed sides of the front belt;

each side brace attachment includes one forward aperture and two rearward apertures; a first substantially linear rod-like member of said side brace frame represents a first side of the forward aperture and a first side of both rearward apertures; a second substantially rod-like member extends from said first rod-like member and represents a second side of both rearward apertures; said forward aperture receives one end of the front belt while said rearward apertures receive the ends of the upper, lower and central belts of the back belts; there being at least one belt received through each aperture so that said side brace attachment provides a means by which the upper, lower, and central belts are maintained spaced apart from one another;

and the back support device can be arranged respective to the wearer thereof whereby the lower belt fits over the hips while the upper belt fits above the small of the spine, and with each belt of the back belt assembly being placed in tension by the front belt, thereby restraining the back in a manner which prevents increased lordosis.

2. The back support of the claim 1 wherein said side brace attachment is a framework having said apertures formed therein, there being one forward aperture for adjustably connecting to one of the opposed sides of the front belt, and adjacent triangular apertures for adjustably connecting to the opposed sides of the upper, lower, and central belts of the back belts.

3. The back support of claim 1 wherein said side brace attachment is a framework having a forwardly directed aperture of rectangular configuration for engaging one of the opposed sides of the front belt, said framework includes two rearwardly directed apertures for engaging one of the opposed sides of each of the upper, lower and central belts; so that the framework orients the apertures in a manner to align the back belt assembly respective to a wearer's back.

4. The back support of claim 1 wherein said side brace attachment is a framework having two rearwardly directed apertures of triangular configuration for adjustably connecting to the individual belts of the back belt support assembly, and a forwardly directed aperture of rectangular configuration for connection to one of the opposed sides of the front belt.

5. The back support of claim 1 wherein said side brace attachment is a framework which includes a relatively large forwardly directed rectangular aperture for engaging one of the opposed marginal ends of the front belt, and which orients the remaining two relatively small apertures of the framework to properly align the individual belts of the back belt assembly respectively to the back of a person who may be wearing the back support; said relatively small apertures represent an isosceles triangle having a base which is common with one side of said rectangular aperture, said isosceles triangle is divided into two right triangles to form said two rearwardly directed apertures.

6. The back support of claim 1 wherein said side brace attachment is in the form of a frame which defines a forwardly directed rectangular aperture within which one said opposed side of the front belt is received therethrough; said side brace attachment further defines a plurality of rearwardly directed apertures which jointly form an isosceles triangle having a base corresponding to one side of the rectangular aperture, and which individually are right triangles;

said central belt and said upper and lower belts of said belt support assembly each include marginal opposed ends, one of which is brought through a rearwardly directed aperture of said side brace attachment to enable each of the marginal ends of each belt to be brought back onto a medial length of the belt in overlapping relationship therewith;

so that said framework can orient the belts of the back belt assembly respective to the wearer's back.

7. An improved antilordosis belt device which is adapted to conform to the lower back and abdomen of a wearer thereof, comprising a flexible relatively wide front belt, a side brace attachment, said front belt has opposed sides which adjustably terminate in attached relationship respective to said side brace attachment;

a plurality of belts which jointly form a back belt assembly and which includes an upper belt of relatively medium width, respective to the front belt, a relatively narrow central and lower belt respectively to the uper belt;

said side brace attachment is a relatively inflexible elongated member which extends along the opposed sides of the front belt; said side brace attachent is in the form of a framework having apertures formed therein, there being a forwardly oriented aperture which receives one of the opposed sides of the front belt, and rearwardly oriented apertures which receive at least one of the opposed sides of the back belt assembly; said upper, central, and lower belts have marginal opposed ends which extend through said rearwardly oriented apertures and are brought back into overlapping engagement, so that each of the belts of the back belt assembly is releasably fastened within an aperture; said forwardly oriented aperture of said side brace attachment is of rectangular configuration; said rearwardly oriented apertures are of triangular configuration having a common side which is perpendicular and integral with one side of the rectangular forwardly oriented aperture;

so that said framework can be positioned to orient the back belt assembly into aligned relationship respective to the back of a person who may be wearing the belt device.

8. An antilordosis belt apparatus which can be worn by a person who seeks to avoid increased lordosis, comprising:

a flexible relatively wide front belt adapted to be placed across the abdomen of the wearer thereof; said front belt is defined by upper and lower opposed horizontal edges and opposed sides;

a plurality of back belts each having opposed sides which terminates in spaced relationship respective to said opposed sides of said front belt;

a side brace attachment which is in the form of a relatively elongated planar frame comprising rod-like members extending along said opposed sides of the front belt; said side brace attachment includes two rearwardly directed apertures of triangular configuration with a common side member which releasably receive one opposed side of a belt of said back belts, a forwardly directed aperture of configuration having a first rod-like side member common with a second rod-like side member of both rearward apertures which receives one opposed side of said front belt so that the belt apparatus can be removed from the wearer thereof;

said plurality of back belts are spaced from one another by the action of said side brace attachments; one of the opposed ends of each of the back belts are joined to one of the opposed sides of the front belt by said side brace attachment;

so that the lowermost belt of the back belts can be received over the hips of a wearer while the uppermost belt of the back belts can be received above the small of the spine of the wearer, with said plurality of belts being placed in tension by the front belt, thereby restraining the back of a wearer in a manner which prevents increased lordosis.

9. The belt apparatus of claim 8 wherein said side brace attachment is in the form of a framework which defines said forwardly directed rectangular aperture forward and rearwardly directed triangular apertures, there being one rectangular aperture for adjustably connecting to each of the opposed sides of the front belt, and a plurality of spaced rearwardly directed triangular apertures for adjustably connecting to one of the opposed sides of each of the back belts.

10. The belt apparatus of claim 9 wherein said forwardly directed rectangular aperture receives a marginal end of the front belt therethrough, with the marginal end of the belt being attached to a medial length thereof, with the remaining apertures aligning the belts of the back belt assembly respective to the back of a person who may be wearing the belt.

11. The belt apparatus of claim 8 wherein one said side brace attachment is arranged to extend along each of the opposed sides of the front belt;

said side brace attachment is a tubular framework, bent into a form which provides said apertures, opposed marginal ends of the back belts are received through the rearwardly directed apertures and are overlapped back onto one another to thereby releasably connect the back belts to the front belt; the combined rearwardly directed triangular apertures geometrically define an isosceles triangle and individually form two right triangles.

* * * * *

UNITED STATES PATENT AND TRADEMARK OFFICE
CERTIFICATE OF CORRECTION

PATENT NO. : 4,459,979
DATED      : JULY 17, 1984
INVENTOR(S) : Royce C. Lewis, Jr.

It is certified that error appears in the above—identified patent and that said Letters Patent is hereby corrected as shown below:

Column 3, line 4, correct the spelling of "assembly";

Column 4, line 56, substitute --belts-- for "belt";

Column 5, line 41, correct the spelling of "attachment";
          Line 68, correct the spelling of "identical";

Column 6, line 4, insert --descent-- after "belts";
          Line 10, substitute --spaces-- for "space";
          Line 26, substitute --sides-- for "side";

Column 7, line 5, substitute --101'-- for "101";
          Line 6, substitute --102'-- for "102";

Column 10, line 21, insert --said-- before "rearwardly".

Signed and Sealed this

Fifth Day of February 1985

[SEAL]

Attest:

DONALD J. QUIGG

Attesting Officer

Acting Commissioner of Patents and Trademarks